(12) United States Patent
Wakita et al.

(10) Patent No.: US 6,448,427 B1
(45) Date of Patent: Sep. 10, 2002

(54) METHOD OF PREPARING AN ORGANOSILICON COMPOUND CONTAINING A METHACRYLOXY FUNCTIONAL GROUP

(75) Inventors: Keiji Wakita; Akihiko Shirahata, both of Chiba Prefecture (JP)

(73) Assignee: Dow Corning Toray Silicone Co., Ltd., Tokyo (JP)

( * ) Notice: Subject to any disclaimer, the term of this patent is extended or adjusted under 35 U.S.C. 154(b) by 0 days.

(21) Appl. No.: 09/994,449

(22) Filed: Nov. 28, 2001

(30) Foreign Application Priority Data

Feb. 22, 2001 (JP) ........................................ 2001-046973

(51) Int. Cl.$^7$ .................................................. C07F 7/08
(52) U.S. Cl. ........................................ 556/440; 556/436
(58) Field of Search ................................... 556/440, 436

(56) References Cited

U.S. PATENT DOCUMENTS

| | | | | |
|---|---|---|---|---|
| 4,946,977 A | | 8/1990 | Bernhardt et al. | 556/440 |
| 5,117,027 A | * | 5/1992 | Bernhardt et al. | 556/440 |
| 5,750,753 A | * | 5/1998 | Kimae et al. | 556/440 |
| 5,789,611 A | * | 8/1998 | Isoyama et al. | 556/440 |
| 6,111,126 A | * | 8/2000 | Tachikawa et al. | 556/440 X |
| 6,197,988 B1 | * | 3/2001 | Okawa et al. | 556/440 |

FOREIGN PATENT DOCUMENTS

| | | |
|---|---|---|
| JP | 52-73826 | 6/1977 |
| JP | 56-104890 | 8/1981 |
| JP | 5-306290 | 11/1993 |
| JP | 42-23332 | 11/1997 |

\* cited by examiner

Primary Examiner—Paul F. Shaver
(74) Attorney, Agent, or Firm—Jennifer S. Warren; Jim L. De Cesare

(57) ABSTRACT

A method of preparing an organosilicon compound containing an acryloxy-functional group or a methacryloxy-functional group represented by general formula $CH_2=CR^1-COO-R^2-Si(OR^3)_nR^4_{3-n}$, where $R^1$, $R^2$, $R^3$, $R^4$ are as described below, comprising reacting (a) an alkali-metal salt of acrylic acid or an alkali-metal salt of methacrylic acid described by general formula $CH_2=CR^1COOM^1$, where $R^1$ is a methyl group or a hydrogen atom and $M^1$ is an alkali metal and (b) an organosilicon containing a halogen-substituted organic group described by general formula $XR^2Si(OR^3)_nR^4_{3-n}$, where X is a halogen atom, $R^2$ is an alkylenoxyalkylene group or an alkylene group comprising 1 to 6 carbon atoms, R3 is an alkyl group comprising 1 to 6 carbon atoms or an alkoxyalkyl group comprising 2 to 4 carbon atoms, $R^4$ is a monovalent hydrocarbon group, and n is an integer of 1 to 3; in the presence of (c) a tertiary amine having a cyclic structure selected from the group consisting of 1,8-diazabicyclo[5.4.0]undec-7-ene, 1,4-diazabicyclo[2.2.2]octane, and 1,5-diazabicyclo[4.3.0]-non-5-ene.

7 Claims, No Drawings

METHOD OF PREPARING AN ORGANOSILICON COMPOUND CONTAINING A METHACRYLOXY FUNCTIONAL GROUP

FIELD OF THE INVENTION

The present invention relates to a new method for easily and efficiently preparing an organosilicon compound containing a methacryloxy-functional group. This method is based on a reaction conducted between an alkali-metal salt of a methacrylic acid and an organosilicon compound with a halogen-substituted organic group in the presence of a phase-transfer catalyst.

BACKGROUND OF THE INVENTION

Japanese Patent Publication (Kokoku) S42-23332 discloses a method of preparing an organosilane compound containing a methacryloxy group by causing a reaction between a solid alkyl salt of a methacrylic acid and a chloroalkyl silane of general formula:

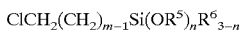

$$ClCH_2(CH_2)_{m-1}Si(OR^5)_nR^6{}_{3-n}$$

where n is an integer between 1 and 3, m is an integer between 1 and 4, and $R^5$ and $R^6$ are alkyl groups having 1 to 4 carbon atoms, the reaction being carried out in the presence of a phase-transfer catalyst such as a tertiary amine or a quaternary ammonium salt.

In the aforementioned publication, the phase-transfer catalysts can be represented by triethylamine, dimethyl aniline, tetramethyl ammonium chloride, benzyltrimethyl ammonium chloride, etc. However, the use of the above phase-transfer catalysts requires that the reaction be carried out at a high temperature of 140 to 180° C. and be extended for about 6 ammonium chloride, etc. However, the use of the above phase-transfer catalysts requires that the reaction be carried out at a high temperature of 140 to 180° C. and be extended for about 6 hours. Furthermore, the reaction may require the use of additional solvents such as dimethylformamide and toluene or xylene. The yield of the obtained organosilane that contains acryloxy-functional groups or methacryloxy-functional groups never exceeds 90% and, in many cases, does not exceed 70%.

Some publications report successful use of the following phase-transfer catalysts for the aforementioned reaction: cyclic polyethers (Japanese Laid-Open Patent Application Kokai S52-73826), quaternary phosphonium salts (Kokai S56-104890), and quaternary ammonium salts with a total number of carbon atoms of from 12 to 40 (Kokai H3-209388). However, all of these catalysts are expensive, have high molecular weight, and in order to achieve high catalytic efficiency have to be used in large quantities. These conditions increase the final cost of the resulting organosilane with acryloxy-functional groups or methacryloxy-functional groups.

Kokai 5-306290 describes a process which involves the reaction of an acrylic acid or a methacrylic acid with an organosilane that contains a halogen-substituted organic group in the presence of a cyclic tertiary-amine compound. However, since this reaction utilizes the aforementioned tertiary amine compound as an adjuvant for hydrogen halide formed in the reaction, the tertiary amine compound has to be used in a stoichiometric quantity, i.e., almost in equivalent mole quantity against the acrylic acid or the methacrylic acid, and the organosilane with halogen-substituted organic groups. The above condition requires the use of additional processes for recovery and regeneration of tertiary amine. Furthermore, quantitative reuse of the tertiary amine presents a problem, and the process becomes economically unjustifiable.

As a result of a study conducted by the present inventors and aimed at the solution of the problems of the prior art, it has been found that, if an alkali metal salt of acrylic acid or an alkali metal salt of methacrylic acid is used as a starting material, a tertiary amine compound having a cyclic structure becomes an extremely efficient phase-transfer catalyst. More specifically, it is an object of the present invention to provide a method of inexpensive production of an organosilicon compound containing an acryloxy-functional group or a methacryloxy-functional group by causing a reaction between an alkali metal salt of acrylic acid or an alkali metal salt of methacrylic acid and an organosilicon compound having a halogen-substituted organic group. The aforementioned phase-transfer catalyst is a relatively inexpensive compound and is used in extremely small quantities and the reaction is characterized by high speed and high yield.

SUMMARY OF THE INVENTION

The present invention is a method of preparing an organosilicon compound containing an acryloxy-functional group or a methacryloxy-functional group represented by general formula

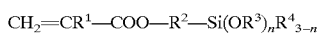

$$CH_2=CR^1-COO-R^2-Si(OR^3)_nR^4{}_{3-n}$$

where $R^1$, $R^2$, $R^3$, $R^4$ are as described below, the method comprises reacting (a) an alkali-metal salt of acrylic acid or an alkali-metal salt of methacrylic acid described by general formula

$$CH_2=CR^1COOM^1,$$

where $R^1$ is a methyl group or a hydrogen atom and $M^1$ is an alkali metal and (b) an organosilicon containing a halogen-substituted organic group described by general formula

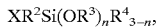

$$XR^2Si(OR^3)_nR^4{}_{3-n},$$

where X is a halogen atom, $R^2$ is an alkylenoxyalkylene group or an alkylene group comprising 1 to 6 carbon atoms, R3 is an alkyl group comprising 1 to 6 carbon atoms or an alkoxyalkyl group comprising 2 to 4 carbon atoms, $R^4$ is a monovalent hydrocarbon group, and n is an integer of 1 to 3;

in the presence of (c) a tertiary amine having a cyclic structure selected from the group consisting of 1,8-diazabicyclo[5.4.0]undec-7-ene, 1,4-diazabicyclo[2.2.2]octane, and 1,5-diazabicyclo[4.3.0]-non-5-ene.

DESCRIPTION OF THE INVENTION

The present invention is a method of preparing an organosilicon compound containing an acryloxy-finctional group or a methacryloxy-fimctional group represented by general formula

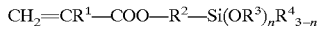

$$CH_2=CR^1-COO-R^2-Si(OR^3)_nR^4{}_{3-n}$$

where $R^1$, $R^2$, $R^3$, $R^4$ are as described below, the method comprises reacting (a) an alkali-metal salt of acrylic acid or an alkali-metal salt of methacrylic acid described by general formula

$$CH_2=CR^1COOM^1,$$

where $R^1$ is a methyl group or a hydrogen atom and $M^1$ is an alkali metal and (b) an organosilicon containing a halogen-substituted organic group described by general formula

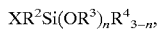
$$XR^2Si(OR^3)_nR^4{}_{3-n},$$

where X is a halogen atom, $R^2$ is an alkylenoxyalkylene group or an alkylene group comprising 1 to 6 carbon atoms, R3 is an alkyl group comprising 1 to 6 carbon atoms or an alkoxyalkyl group comprising 2 to 4 carbon atoms, $R^4$ is a monovalent hydrocarbon group, and n is an integer of 1 to 3;

in the presence of (c) a tertiary amine having a cyclic structure selected from the group consisting of 1,8-diazabicyclo[5.4.0]undec-7-ene, 1,4-diazabicyclo[2.2.2]octane, and 1,5-diazabicyclo[4.3.0]-non-5-ene.

Component (a) of the present invention is an alkali-metal salt of acrylic acid or an alkali-metal salt of methacrylic acid described by general formula

$$CH_2=CR^1COOM^1,$$

where $R^1$ is a methyl group or a hydrogen atom and $M^1$ is an alkali metal. Component (a) is represented by the following specific compounds: sodium methacrylate, potassium methacrylate, sodium acrylate, and potassium acrylate.

The aforementioned component (a) can be produced by neutralizing an acrylic acid or a methacrylic acid with sodium or potassium hydroxide or by saponifying a methyl acrylate or a methyl methacrylate with a sodium or potassium hydroxide. The alkali metal salt of acrylic acid or the alkali metal salt of methacrylic acid can be used in the reaction in a solid state or in a liquid state as a dispersion or a solution in an appropriate solvent.

Component (b) is an organosilicon containing a halogen-substituted organic group described by general formula

$$XR^2Si(OR^3)_nR^4{}_{3-n},$$

where X is a halogen atom, preferably chlorine or bromine. $R^2$ is an alkylenoxy-alkylene group or an alkylene group having 1 to 6 carbon atoms. The following are examples of such groups: methylene, ethylene, methylmethylene, propylene, methylethylene, butylenes, hexylene, 1-methylpentylene, 1,4-dimethylbutylene, or a similar alkylene group; methylene-oxypropylene, methylene-oxypentylene or a similar alkylene-oxyalkylene group. Most preferable among the above are methylene, propylene, butylenes, methylene-oxypropylene, and methylene-oxypentylene groups, and especially propylene groups. R3 is an alkyl group comprising 1 to 6 carbon atoms or an alkoxyalkyl group having 2 to 4 carbon atoms, $R^4$ is a monovalent hydrocarbon group, and n is an integer of 1 to 3. The following are examples of alkyl groups suitable for $R^3$: methyl, ethyl, propyl, butyl, pentyl, isopropyl, isobutyl, cyclopentyl, and cyclohexyl groups. Examples of alkoxyalkyl groups represented by $R^3$ are methoxyethyl, methoxypropyl, and methoxybutyl groups. Most preferable of the above $R^3$ groups are methyl, ethyl, and methoxyethyl groups. $R^4$ is a monovalent hydrocarbon group such as a methyl, ethyl, propyl, butyl, pentyl, isopropyl, isobutyl, cyclopentyl, cyclohexyl, or a similar alkyl group; a phenyl, tolyl, xylyl, naphthyl, or a similar aryl group; a vinyl, allyl, butenyl, pentenyl, hexenyl, or a similar alkenyl group; a benzyl, phenethyl, or a similar aralkyl group. Most preferable $R^4$ is a methyl group. Subscript "n" is an integer of from 1 to 3.

It is preferred to use the following organosilicon compounds having halogen-substituted organic groups: chloromethyldimethylmethoxysilane, γ-chloropropyltrimethoxysilane, γ-chloropropyltris-(methoxyethoxy)silane, γ-chloropropylmethyldimethoxysilane, γ-chloropropylbutyldimethoxysilane, δ-chlorobutyltrimethoxysilane, δ-chlorobutylmethyldimethoxysilane, δ-chlorobutyl-tris-(methoxyethoxy)silane, γ-bromopropyltrimethoxysilane, γ-bromopropyltriethoxysilane, bromopropyltris-(methoxyethoxy)silane, γ-bromopropylmethyldimethoxysilane, or the like. Among these compounds most preferable are γ-chloropropyltrimethoxysilane, γ-chloropropyltriethoxysilane, γ-chloropropyl tris-(methoxyethoxy)silane, γ-chloropropylmethyldimethoxysilane, especially, γ-chloropropyltrimethoxysilane and γ-chloropropylmethyldimethoxysilane.

The tertiary amine with a cyclic structure, which constitutes component (c), is known in the art in various types. However, the following tertiary amines are preferable for the present invention: 1,8-diazabicyclo[5.4.0]undec-7-ene, 1,4-diazabicyclo [2.2.2]octane, and 1,5-diazabicyclo[4.3.0]-non-5-ene. Among these, most suitable is 1,8-diazabicyclo [5.4.0]undec-7-ene (hereinafter referred to as DBU), as it is least expensive and is readily available on the market.

It is recommended that the present reaction be carry out with the use of components (a) and (b) in an amount of 0.1 to 2 mole, preferably 0.15 to 1.5 mole of the alkali metal salt of acrylic acid or the alkali metal salt of methacrylic acid (component (a)), based on 1 mole of the organosilicon that contains a halogen-substituted organic group (component (b)).

The tertiary amine (c) with a cyclic structure, which is used as a phase-transfer catalyst, should be added in an amount of 0.0001 to 0.05 mole, preferably 0.001 to 0.01 mole, based on 1 mole of the alkali metal salt of acrylic acid or the alkali metal salt of methacrylic acid (component (a)). The reaction should be carried out at a temperature of 30° C. to 180° C., preferably of 80° C. to 130° C. The reaction time may differ depending on the type of the aforementioned alkali metal salt of acrylic acid or the alkali metal salt of methacrylic acid, amount of the catalyst used in the reaction, etc., but normally the reaction may last from 10 min. to several tens of hours.

Although there are no specific requirements for the use of a solvent, the method of the invention can be carried out with a solvent. In some cases the organosilicon (b) that contains a halogen-substituted orgaic group may be used as both a reaction substrate and a solvent. The solvent can be represented by benzene, toluene, xylene, or a similar aromatic-type solvent; methanol, ethanol, or a similar alcohol-type solvent; or methylformamide, or another solvent neutral to the starting materials and the catalyst.

In order to prevent polymerization during the reaction and distillation, the composition may contain conventional polymerization inhibitors such as a phenol compound represented by methoxyphenol and 2,6-di-t-butyl-4-methylphenol, phenothiazine, an amine-type compound, or a sulfur-containing compound.

Compounds which contain acryloxy functional groups or methacryloxy functional groups and are produced by the present method are described by general formula

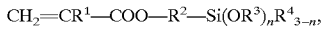
$$CH_2=CR^1—COO—R^2—Si(OR^3)_nR^4{}_{3-n},$$

where $R^1$, $R^2$, $R^3$, $R^4$ are the same as defined above. The following are examples of such compounds:

methacryloxymethyldimethylmethoxysilane,
γ-methacryloxypropylmethydimethoxysilane,
γ-methacryloxypropyltrimethoxysilane,
γ-methacryloxypropyltriethoxysilane,
γ-methacryloxypropyl-tris-(methoxyethoxy)silane,
γ-methacryloxybutyl dimethoxysilane, δ-methacryloxybutyl trimethoxysilane,
δmethacryloxybutylmethyldimethoxysilane,
δ-methacryloxybutyltris-(methoxyethoxy)silane;
acryloxymethyldimethylmethoxysilane,
γ-acryloxypropylmethyldimethoxysilane,
γacryloxypropyltrimethoxysilane,
γ-acryloxypropyltriethoxysilane, γ-acrylopxypropyl-tris-(methoxyethoxy)silane,
γ-acryloxypropylbutyldimethoxysilane,
δ-acryloxybutyltrimethoxysilane,
δ-acryloxybutylmethyldimethoxysilane, δ-acryloxybutyl-tris-(methoxyethoxy)silane, etc.

EXAMPLES

The invention will be further described with reference to specific examples, which, however, should not be construed as limiting the scope of application of the invention.

Practical Example 1

A 100-ml three-neck flask equipped with a reflux cooling tube, stirrer, and thermometer was loaded with 12.4 g (0.1 mole) potassium methacrylate, 29.8 g (0.15 mole) of γ-chloropropyltrimethoxysilane, 0.12 g (0.0008 mole) of 1,8-diazabicyclo[5.4.0]undec-7-ene as catalyst (DBU), and 7 mg of a polymerization inhibitor in the form of phenothiazine. The components were then stirred for 2 hours at 105° C. Analysis by gas chromatography (GC) showed that the reaction produced 23.8 g of γ-methacryloxypropyltrimethoxysilane. The yield of the product was 96% based on potassium methacrylate.

Comparative Example 1

A reaction was carried out under the same conditions as in Practical Example 1, except that 0.15 g (0.0005 mole) of a quaternary ammonium salt in the form of brominated tetrabutyl ammonium was used as a catalyst instead of DBU. The yield of γ-methacryloxypropyltrimethoxysilane after 2-hour reaction was 30%, and after 4-hour reaction less than 64%.

Comparative Example 2

A reaction was carried out under the same conditions as in Practical Example 1, except that 0.22 g (0.0005 mole) of a quaternary ammonium salt in the form of chlorinated trioctyl methyl ammonium was used as a catalyst instead of DBU. The yield of γ-methacryloxypropyltrimethoxysilane after 2-hour reaction was 33%, and after 6-hour reaction less than 67%.

Practical Example 2

A reaction was carried out similar to Practical Example 1 with the use of 10.8 g (0.1 mole) sodium methacrylate, 29.8 g (0.15 mole) γ-chloropropyl trimethoxysilane, 0.08 g (0.0005 mole) DBU as a catalyst, 7 mg phenothiazine, and 10 ml toluene for 2 hours at 105° C. Analysis by GC showed that the reaction produced 23.3 g of γ-methacryloxypropyltrimethoxysilane. The yield of the product was 94% based on sodium methacrylate.

Comparative Example 3

A reaction was carried out under the same conditions as in Practical Example 2, except that 0.21 g (0.0005 mole) of a quaternary ammonium salt in the form of chlorinated trioctyl methyl ammonium was used as a catalyst instead of DBU. The yield of γ-methacryloxypropyltrimethoxysilane after a 2-hour reaction was 37%, and after 6-hour reaction less than 38%.

Practical Example 3

A reaction was carried out under the same conditions as in Practical Example 1, except that amount of DBU used as a catalyst was reduced to 0.03 g (0.0002 mole). The yield of γ-methacryloxypropyltrimethoxysilane after a 2-hour reaction was 34%, but after 6 hour reaction reached a high value of 95%.

Practical Example 4

A reaction was carried out under the same conditions as in Practical Example 1, except that 0.06 g (0.0005 mole) of 1.5-diazabicyclo[4.3.0]-non-5-ene were used as a catalyst. The yield of γ-methacryloxypropyl trimethoxysilane after a 2-hour reaction was 93%.

Practical Example 5

A reaction was carried out similar to Practical Example 1 at 105° C. for 2 hours with a mixture consisting of 12.4 g (0.1 mole) potassium methacrylate, 27.4 g (0.15 mole) γ-chloropropylmethyldimethoxysilane, 0.08 g (0.0005 mole) DBU as a catalyst, and 7 mg phenothiazine as a polymerization inhibitor. Analysis by GC showed that the reaction produced 22.5 g of γ-methacryloxypropyl-methyldimethoxysilane. The yield of the product was 97% based on potassium methacrylate.

Practical Example 6

A reaction was carried out similar to Practical Example 1 at 105° C. for 2 hours with a mixture consisting of 12.4 g (0.1 mole) potassium methacrylate, 36.1 g (0.15 mole) γ-chloropropyltriethoxysilane, 0.08 g (0.0005 mole) DBU as a catalyst, and 7 mg phenothiazine as a polymerization inhibitor. Analysis by GC showed that the reaction produced 27.9 g of γ-methacryloxypropyltriethoxysilane. The yield of the product was 96% based on potassium methacrylate.

Practical Example 7

A reaction was carried out similar to Practical Example 1 at 105° C. for 2 hours with a mixture consisting of 9.4 g (0.1 mole) sodium acrylate, 29.8 g (0.15 mole) γ-chloropropyltrimethoxysilane, 10 ml toluene, 0.08 g (0.0005 mole) DBU as a catalyst, and 7 mg phenothiazine as a polymerization inhibitor. Analysis by GC showed that the reaction produced 22.3 g of γ-acryloxypropyltrimethoxysilane. The yield of the product was 95% based on sodium acrylate.

We claim:

1. A method of preparing an organosilicon compound containing a methacryloxy-functional group described by general formula

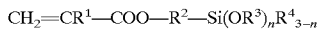
$$CH_2=CR^1-COO-R^2-Si(OR^3)_nR^4_{3-n}$$

where $R^1$, $R^2$, $R^3$, $R^4$ are as described below, comprising reacting (a) an alkali-metal salt of a methacrylic acid described by general formula

$$CH_2=CR^1COOM^1,$$

where $R^1$ is a methyl group or a hydrogen atom and $M^1$ is an alkali metal and (b) an organosilicon containing a halogen-substituted organic group described by general formula $$XR^2Si(OR^3)_nR^4_{3-n},$$

where X is a halogen atom, $R^2$ is an alkylenoxyalkylene group or an alkylene group comprising 1 to 6 carbon atoms, $R^3$ is an alkyl group or an alkoxyalkyl group comprising 2 to 4 carbon atoms, $R^4$ is a monovalent hydrocarbon group, and n is an integer of 1 to 3; in the presence of (c) a tertiary amine having a cyclic structure selected from the group consisting of 1,8-diazabicyclo[5.4.0]undeca-7-en, 1,4-diazabicyclo[2.2.2]octane, and 1,5-diazabicyclo[4.3.0]-nona-5-en; and wherein the alkali-metal salt of a methacrylic acid of component (a) and the tertiary amine of component (c) having a cyclic structure are added in a mole ratio (a) to (c) of 1:0.001 to 1:0.0 1; or wherein the alkali-metal salt of a methacrylic acid of component (a) and the tertiary amine of component (c) having a cyclic structure are added in a mole ratio (a) to (c) of 1:0.0001 to 1:0.05.

2. The method of preparing an organosilicon compound containing a methacryloxy-functional group according to claim 1 where component (b) is selected from the group consisting of γ-chloropropyltrimethoxysilane and γ-chloropropylmethyldimethoxysilane.

3. The method of preparing an organosilicon compound containing a methacryloxy-functional group according to claim 1 where component (a) is selected from the group consisting of sodium methacrylate, potassium methacrylate, sodium acrylate, and potassium acrylate.

4. The method of preparing an organosilicon compound containing a methacryloxy-functional group according to claim 1 where X is a chlorine or bromine atom.

5. The method of preparing an organosilicon compound containing a methacryloxy-functional group according to claim 1 where component (c) is 1,8-diazabicylo[5.4.0] undec-7-ene.

6. The method of preparing an organosilicon compound containing a methacryloxy-functional group according to claim 1 where the mole ratio of component (a) to component (b) added to the method is 0.1 to 2.

7. The method of preparing an organosilicon compound containing a methacryloxy-functional group according to claim 1 where the mole ratio of component (a) to component (b) added to the method is 0.15 to 1.5.

* * * * *